(12) United States Patent
Hardesty

(10) Patent No.: US 7,526,065 B2
(45) Date of Patent: Apr. 28, 2009

(54) VOLUMETRIC X-RAY IMAGING SYSTEM WITH AUTOMATIC IMAGE RESOLUTION ENHANCEMENT

(75) Inventor: Dan Hardesty, Lincoln, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/907,747

(22) Filed: Apr. 14, 2005

(65) Prior Publication Data

US 2005/0169428 A1 Aug. 4, 2005

Related U.S. Application Data

(63) Continuation-in-part of application No. 10/644,206, filed on Aug. 20, 2003.

(51) Int. Cl.
*G01N 23/083* (2006.01)
*H05G 1/64* (2006.01)
*G21K 1/04* (2006.01)

(52) U.S. Cl. .................. 378/62; 378/98.7; 378/145; 378/151; 378/189; 378/197

(58) Field of Classification Search ............ 378/4, 378/8, 16, 19, 95, 97, 108–112, 151, 62, 378/98.7, 98.8, 98.9, 98.11, 146, 150, 197, 378/145, 189; 600/429
See application file for complete search history.

(56) References Cited

U.S. PATENT DOCUMENTS

| | | | |
|---|---|---|---|
| 5,278,887 A | 1/1994 | Chiu et al. | |
| 5,282,254 A | 1/1994 | Chiu et al. | |
| 5,369,678 A | 11/1994 | Chiu et al. | |
| 6,052,476 A | 4/2000 | Qian et al. | |
| 6,055,295 A * | 4/2000 | Murthy et al. | 378/151 |
| 6,094,468 A | 7/2000 | Wilting et al. | |

(Continued)

FOREIGN PATENT DOCUMENTS

DE 199 50 794 A1 6/2001

(Continued)

OTHER PUBLICATIONS

Fred Behlen, et al., Report of the Working Group on Digital Mammography: Digital Displays and Workstation Design, Public Health Service's Office on Women's Health and National Cancer Institute, Mar. 9-10, 1998, pp. 1-29.

(Continued)

*Primary Examiner*—Allen C. Ho
(74) *Attorney, Agent, or Firm*—Vedder Price P.C.

(57) ABSTRACT

An automated X-ray imaging system and method for producing a plurality of X-ray imaging signals having selectively enhanced volumetric image resolutions, e.g., for magnifying the field of view and providing a volumetric display image having features not otherwise visible to an unaided human eye. Successive doses of X-ray radiation are applied to a portion of the subject to produce corresponding volumetric image signals. Such doses of X-ray radiation are controlled by controlling X-ray radiation characteristics, such as intensity, focal spot size, focal spot location, focal spot shape, or collimation, to cause a subsequent volumetric image signal to differ from a prior volumetric image signal in one or more volumetric image characteristics, such as volumetric image resolution.

10 Claims, 7 Drawing Sheets

U.S. PATENT DOCUMENTS

| | | | |
|---|---|---|---|
| 6,196,715 B1 | 3/2001 | Nambu et al. | |
| 6,215,848 B1 | 4/2001 | Linders et al. | |
| 6,292,534 B1 | 9/2001 | Linders et al. | |
| 6,317,617 B1 | 11/2001 | Gilhuijs et al. | |
| 6,324,243 B1* | 11/2001 | Edic et al. | 378/4 |
| 6,463,121 B1 | 10/2002 | Milnes | |
| 6,480,565 B1 | 11/2002 | Ning | |
| 6,501,828 B1* | 12/2002 | Popescu | 378/150 |
| 6,535,821 B2* | 3/2003 | Wang et al. | 702/19 |
| 6,594,339 B1 | 7/2003 | Alving et al. | |
| 6,814,489 B2* | 11/2004 | Jensen et al. | 378/197 |
| 6,901,156 B2 | 5/2005 | Giger et al. | |
| 7,085,343 B2 | 8/2006 | Shinno et al. | |
| 7,113,569 B2* | 9/2006 | Okumura et al. | 378/150 |
| 2003/0099328 A1 | 5/2003 | Jensen et al. | |
| 2006/0140339 A1* | 6/2006 | Marcovitch | 378/20 |

FOREIGN PATENT DOCUMENTS

| | | |
|---|---|---|
| EP | 1 092 391 A1 | 7/2001 |

OTHER PUBLICATIONS

European Supplemental Search Report for European Patent Application No. EP04778772, dated Mar. 8, 2007, 2 pages.

International Search Report for PCT/US04/23419, dated Mar. 11, 2005, 1 page.

Dorf, Richard C., "Modern Control Systems", Addison-Wesley Series in Electric Engineering, 1967.

* cited by examiner

VOLUMETRIC X-RAY IMAGING SYSTEM WITH AUTOMATIC IMAGE RESOLUTION ENHANCEMENT

RELATED APPLICATIONS

This is a continuation-in-part of U.S. patent application Ser. No. 10/644,206, filed Aug. 20, 2003, and entitled "X-Ray Imaging System With Automatic Image Resolution Enhancement".

BACKGROUND OF THE INVENTION

The present invention relates to x-ray imaging systems, and in particular, to automated x-ray imaging systems capable of providing selectively enhanced volumetric image resolutions, e.g., for magnifying the field of view and providing a volumetric display image having features not otherwise visible to an unaided human eye.

Medical x-ray imaging has been and continues to be a very important tool for medical diagnostics. Such systems typically use x-ray film or digital electronic image sensors to record the intensity of the photons that pass through the subject. Conventional automatic exposure systems are often used to control the x-ray exposure by controlling things such as the voltage or current driving the x-ray source or controlling the exposure time to achieve the best exposure to the entire volume of the subject being imaged. Such systems use a signal acquired at the exit side of the subject of the x-ray imaging to control the exposure. In those systems using film, detectors, placed either in front of or behind the film, generate one or more signals based on the amount of x-ray exposure received. These detectors, calibrated to the film being used, provide signals which can be processed to determine and control the overall exposure. In those systems using electronic image sensors, the image signals provided by the sensor array can be used directly for monitoring the exposure and providing appropriate control signals.

Following completion of the x-ray imaging itself, the image in its film or electronic form is then typically checked for image quality by the attending technician. Later, that same film or electronic image is checked by a specialist, e.g., a radiologist, and a diagnosis is performed. Depending upon the results of the diagnosis, the subject may be brought back for additional x-ray imaging of the region or regions found to be of greater interest following the diagnosis. Such subsequent imaging will typically be performed with the collimator adjusted to focus on the specific regions of interest, and increased x-ray doses will be applied.

Images generated using x-ray radiation are often degraded by scattering of the radiation, low signal-to-noise ratio (caused by a desire for exposing the subject to as minimum a radiation dose as possible), requirements for large dynamic range, and saturation of the sensors used in the detector array (caused by x-ray radiation striking the imager without attenuation). While these problems can be minimized by the attending technician using collimators to isolate a region of interest, such technician is generally not qualified to read the images or determine the appropriate areas of interest. Further, during many procedures, the patient is under some discomfort during the procedure and is, therefore, removed from the imaging system prior to any reading of the film or image. Accordingly, significant percentages of subjects are recalled for additional imaging.

These types of problems become increasingly significant as the sizes and scales of the features sought to be viewed decrease. For example, a number of studies have revealed the role of angiogenesis, i.e., the formation and differentiation of blood vessels, in the development of cancer and other diseases. Corresponding trials with antiangiogenic approaches to treatment have been used with some success. Accordingly, techniques for evaluating tissue vascularization have become increasingly important. The well-known technique of computed tomography (CT) and magnetic resonance imaging (MRI) have been used most frequently to evaluate tumor malignancy and the effects of various therapies on the patients. Typically, contrast enhancement materials are used for purposes of improving the resulting images. However, accurate imaging of the blood vessels present has relied primarily upon estimations based on the accumulation of the contrast medium within the small spaces among the vessels, generally as a result of increased vessel leakage. Further, the small sizes of the blood vessels within the tumors are difficult to assess with typical scanner equipment due to low sensitivity of the contrast media and low signal-to-noise ratio (SNR) when using high local resolution scanning. These problems can often be overcome by using micro-CT (e.g., using a synchrotron source providing an intense collimated beam of monochromatic x-rays) or volumetric CT (e.g., using multiple flat panel detectors or multiple rows of detectors to scan a volume of the subject). However, the problems discussed above concerning real-time evaluation and focusing upon the region of interest remain.

Accordingly, it would be desirable to have an x-ray imaging system capable of determining, focusing upon and selectively increasing, in a real time manner, the volumetric image resolution of the regions of the subject being of the most interest.

SUMMARY OF THE INVENTION

In accordance with the presently claimed invention, an automated X-ray imaging system and method are provided for producing a plurality of X-ray imaging signals having selectively enhanced volumetric image resolutions, e.g., for magnifying the field of view and providing a display image having features not otherwise visible to an unaided human eye. Successive doses of X-ray radiation are applied to a portion of the subject to produce corresponding image signals. Such doses of X-ray radiation are controlled by controlling X-ray radiation characteristics, such as intensity, focal spot size, focal spot location, focal spot shape, or collimation, to cause a subsequent image signal to differ from a prior image signal in one or more image characteristics, such as planar or volumetric image characteristics including planar and volumetric image resolutions.

In accordance with one embodiment of the presently claimed invention, an automated X-ray imaging system for producing a plurality of X-ray imaging signals includes an X-ray emission system, an X-ray detection system and a control system. The X-ray emission system is responsive to at least one emission control signal by providing at least first and second doses of X-ray radiation, wherein the second dose differs from the first dose in one or more of a plurality of X-ray radiation characteristics. The X-ray detection system is responsive to at least one detection control signal and is for placement in relation to the X-ray emission system to be responsive to at least respective portions of the first and second doses of X-ray radiation following exposure thereto of at least a portion of a subject disposed substantially between the X-ray emission and detection systems by providing corresponding first and second image signals corresponding to the respective portions of the first and second doses of X-ray radiation, respectively. The control system, coupled to the X-ray emission and detection systems, is responsive to the first and second image signals by providing the emission and detection control signals, wherein the second volumetric image signal differs from the first image signal in one or more of a plurality of image characteristics, and the first and second image signals together form a plurality of images which is one or more of: a planar image and a volumetric image, respectively; a volumetric image and a planar image, respectively; a lower resolution image and a higher resolution image, respectively; and a higher resolution image and a lower resolution image, respectively.

In accordance with another embodiment of the presently claimed invention, an automated method for producing a plurality of X-ray imaging signals includes:

receiving at least one emission control signal;

generating, in response to the at least one emission control signal, at least first and second doses of X-ray radiation, wherein the second dose differs from the first dose in one or more of a plurality of X-ray radiation characteristics;

receiving at least a portion of the first and second doses of X-ray radiation following exposure thereto of at least a portion of a subject;

receiving at least one detection control signal;

generating, in response to said at least one detection control signal and said at least respective portions of said first and second doses of X-ray radiation, first and second image signals corresponding to said respective portions of said first and second doses of X-ray radiation, respectively;

processing said first and second image signals; and generating, in response to the processed first and second image signals, the emission and detection control signals, wherein the second image signal differs from the first image signal in one or more of a plurality of image characteristics, and the first and second image signals together form a plurality of images which is one or more of: a planar image and a volumetric image, respectively; a volumetric image and a planar image, respectively; a lower resolution image and a higher resolution image, respectively; and a higher resolution image and a lower resolution image, respectively.

DETAILED DESCRIPTION OF THE INVENTION

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

As discussed in more detail below, an x-ray imaging system in accordance with the presently claimed invention improves diagnostic x-ray image quality by using real-time computer analysis of an initial image, following which multiple images of regions of interest are taken using optimized imaging parameters. Optimization of the x-ray parameters includes collimation of the x-ray beam to the region of interest, as well as controlling focal spot size, focal spot location, focal spot shape, x-ray tube voltage or current, and bias or dynamic range of the detector.

Figure 1:
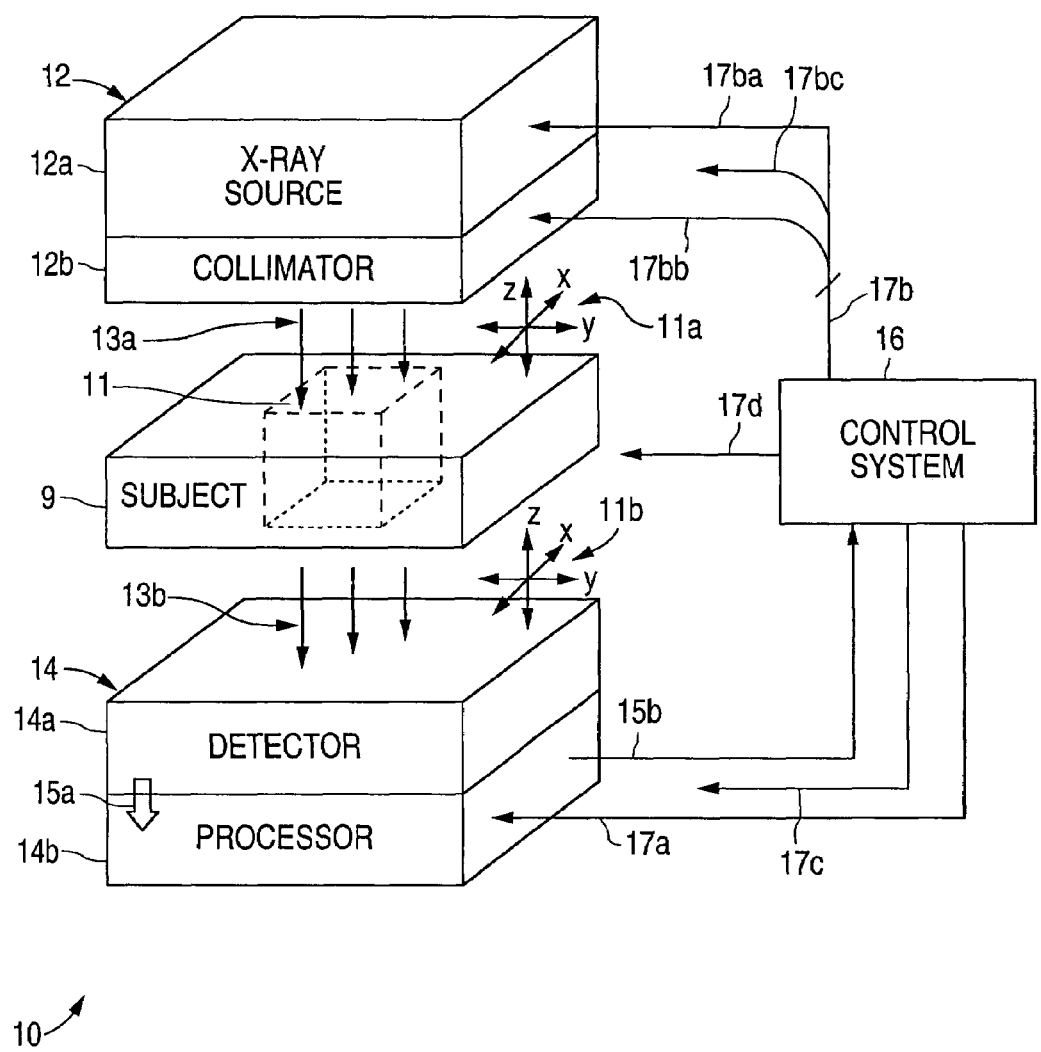
FIG. 1 is a functional block diagram of an x-ray imaging system in accordance with one embodiment of the presently claimed invention.

Referring to FIG. 1, an x-ray imaging system 10 in accordance with one embodiment of the presently claimed invention includes an x-ray transmitter 12 and an x-ray detector 14, between which the subject 9 for the image is to be placed. Such components 12, 14 are conventional in nature. For example, the x-ray transmitter 12 will include an x-ray radiation source 12a, such as an x-ray tube, which is well-known in the art. Additionally, a controllable collimator 12b is used, as discussed in more detail below, to collimate, i.e., focus, the emitted x-ray radiation 13a to which the subject 9 is exposed.

The resulting x-ray radiation 13b which exits the subject is detected by a conventional detector assembly 14a which produces corresponding pixel signals 15a which are processed by the processor 14b into image signals 15b.

Figure 2A:
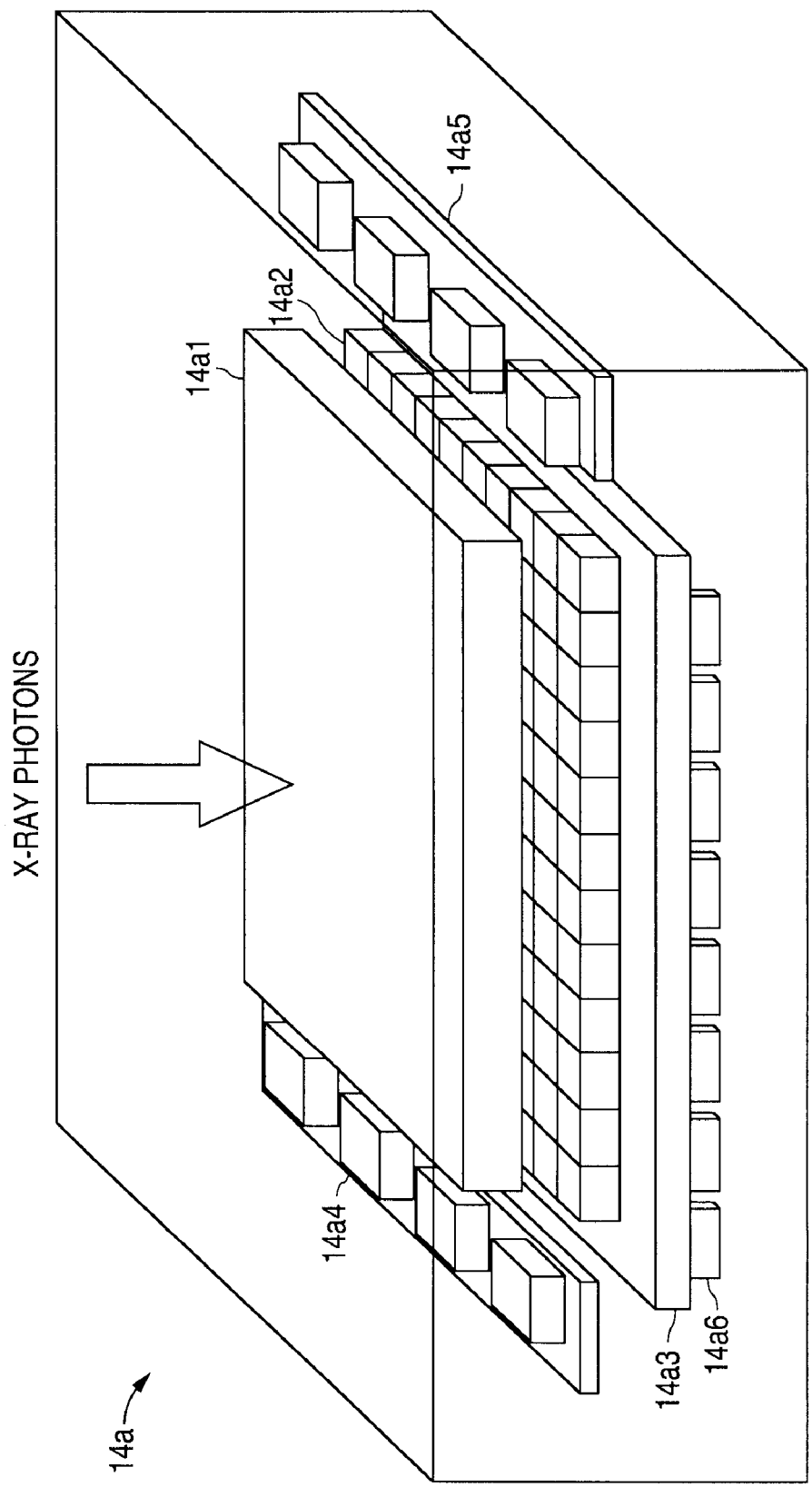
FIG. 2A is a functional block diagram of a control system of FIG. 1.

Referring to FIG. 2A, such detector assemblies 14a are well known in the art, often in the form of a detector cassette, or receptor, 14a which is similar in external appearance to the typical cassette which contains standard medical X-ray film and is, therefore, highly mobile and easy to use as required for a radiographic mode of operation. A scintillation layer 14a1, e.g. of cesium iodide (CsI), absorbs and converts impinging X-ray photons to visible light photons for detection by photosensitive elements within the detector array 14a2, e.g. of amphorphous silicon (a-Si). The thickness of the scintillation layer 14a1 is selected so as to absorb sufficient X-ray photons and produce sufficient visible photons so at to generate an adequate SNR for fluoroscopic operation. Similarly, the columns, or "needles", of the crystalline CsI are selected so as to have diameters sufficiently small to support the spatial resolution sampling desired for radiographic operation.

The detector array 14a2 is designed in accordance with well known techniques into a two dimensional array of microscope squares referred to as picture elements, or "pixels." Each pixel is composed of an addressable photosensitive element, such as a photodiode and switching transistor combination. Each pixel is accessed in accordance with drive signals from off-array driver circuit assemblies 14a4, 14a5 which provide addressing control signals. In accordance with well known techniques, the lateral dimensions of the photodiodes are made sufficiently small to provide the desired spatial resolution imaging for radiographic operation and the capacitance of the photodiodes is designed to be sufficiently large to provide the desired signal handling capacity for accommodating the largest signal produced during radiographic operation.

The pixel data accessed by the driver circuits 14a4, 14a5 are read out by a receiver, or readout, circuit assembly 14a6. The receiver circuit assembly 14a6 and detector array 14a2 are mounted on opposing sides of a base plate 14a3. (The receiver circuit assembly 14a6 is placed beneath the array 14a2 so as to minimize the lateral size of the detector cassette 14a and thereby make the detector cassette 14a approximately the same size as a film cassette. If so desired, the driver circuits 14a4, 14a5 can also be placed beneath the array 14a2.) (Further discussion of an x-ray imaging system using such a detector assembly can be found in U.S. Pat. No. 5,970,115, entitled "Multiple Mode Digital X-ray Imaging System", the disclosure of which is incorporated herein by reference.)

Additionally, in accordance with the presently claimed invention, a control system 16 is used which, as discussed in more detail below, processes the image signals 15b to determine regions of interest within the subject. Once such region or regions of interest have been identified, the control system 16 provides appropriate detector control signals 17a and x-ray control signal 17b, which include specific control signal 17ba, 17bb for the x-ray source 12a and collimator 12b.

Figure 2B:
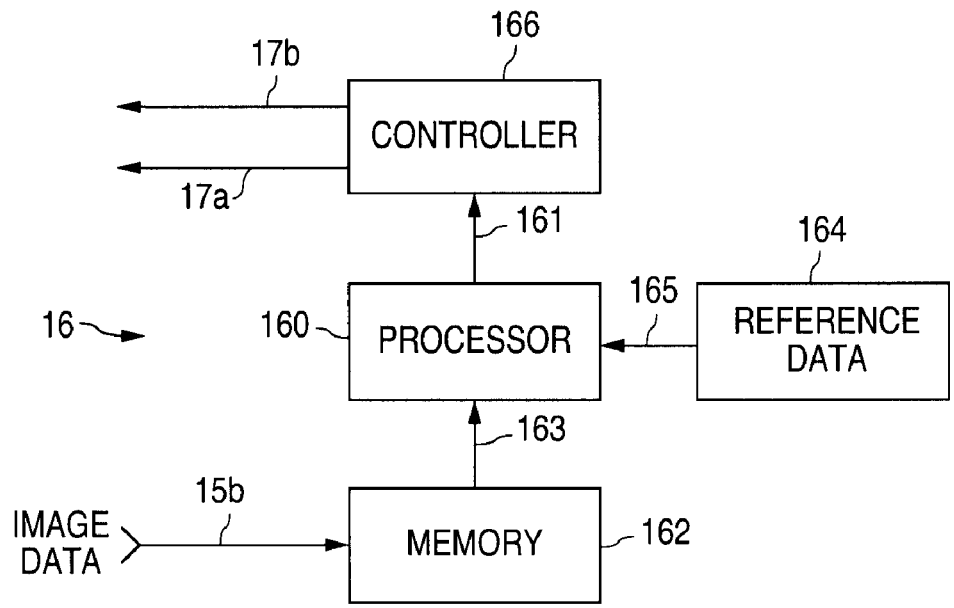
FIG. 2B is a functional block diagram of a control system of FIG. 1.

Referring to FIG. 2, the control system 16 includes a processor 160, memory 162 for the incoming image data 15b, memory 164 for reference image data, and a controller 166 for generating the control signals 17a, 17b for the detector 14 and x-ray transmitter 12, all interconnected substantially as shown. The incoming image data 15b from the detector assembly 14 is stored in a memory 162. The stored memory data 163 is processed by the processor 160 in conjunction with reference image data 165 stored in the reference data memory 164.

Such processing by the processor 160 can be performed in accordance with well known image analysis techniques. For example, the reference data 165 can include data representing or corresponding to any of a number of well known characteristics known to be commonly associated with various medical conditions. For example, such data 165 can represent characteristics commonly associated with breast cancer, including microcalcification clusters, masses or architectural distortions. In the case of microcalcification clusters, the image data 163 may contain image data showing clusters of bright spots, suggestive of microcalcification clusters. Such image data 163 can then, in real time, be compared against and processed with the reference data 165, e.g., using neural network processing or artificial intelligence techniques. In the event that the result of such processing suggests that such a feature exists, that portion of the image data 163 can be identified as a region of interest for which control signals 17a, 17b are to be generated so as to access more detailed image data 15b. Similarly, in the case of masses or architectural distortions, the image data 163 can be compared against and processed with the reference data 165 to determine whether the image data 163 contains data suggestive of such features. If so, the corresponding region(s) of interest can be identified, and appropriate control signals 17a, 17b can be generated for producing, in real time, more detailed and enhanced image data 15b.

Once the stored image 163 and reference 165 data have been processed, and a region of interest within the subject has been identified, control data 161 is provided by the processor to the controller 166, which then provides appropriate control signals 17a, 17b for the detector assembly 14 and x-ray transmitter 12. This process can be repeated until an image of sufficient resolution is produced, e.g., with sufficiency of the resolution being determined either by the user in real time during the imaging process (e.g., by viewing the displayed image), or by the controller 166 based upon whether further processing (e.g., comparison) of the incoming image data 15b (as represented by the stored image data 163) with the reference data 165 yields any further image information beyond some predetermined minimum.

Figure 3:
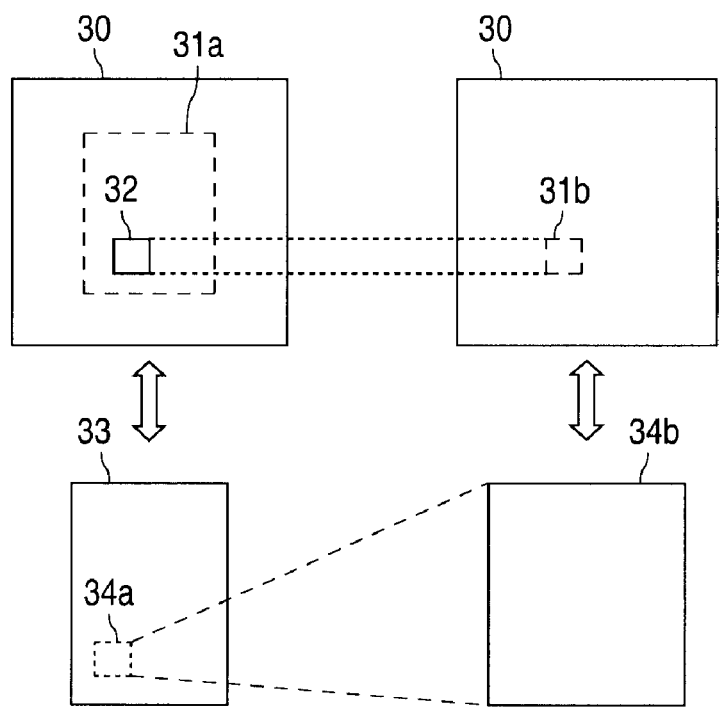
FIG. 3 is a diagram depicting the selective collimation and resulting image resolution enhancement using an x-ray imaging system in accordance with the presently claimed invention.

Referring to FIG. 3, the effect of image resolution enhancement in accordance with the presently claimed invention can be better understood. During initial exposure of the subject 9 to x-ray radiation 13a, the otherwise normal full field of view 30 for the imaging system is restricted to a smaller field 31a by use of the collimator 12b in accordance with well-known principles. This collimated image field 31a produces image data 15b representing an image 33 corresponding to such collimated field 31a. Based upon processing within the control system 16, a region of interest 32 is identified within the collimated field 31a. Such region of interest 32 corresponds to image data 15b representing a particular region 34a within the image 33. Accordingly, the processor 160 produces control data 161 for the controller 166 to produce appropriate control signals 17a, 17b for the detector assembly 14 and x-ray radiation transmitter 12. In accordance with well-known imaging system control techniques, such control signals 17a, 17b can be used to control biasing or dynamic range of the detector assembly 14, as well as voltage or current driving the x-ray tube within the x-ray source 12a, control signals for the focal spot (e.g., size, location or shape) within the x-ray source 12a, and collimation of the transmitted x-ray radiation 13a.

Based upon control signals 17bb to the collimator 12b, further collimation may be performed such that the collimated field 31b is reduced to focus exclusively on the identified region of interest. With such increased collimation, as well as other modifications to the imaging parameters, as discussed above, the resolution of the identified region of interest 34a is accordingly increased to produce image data representing an image 34b having enhanced resolution.

Referring back to FIG. 1, the extent of the control that can be provided by the control system 16 over the x-ray radiation transmitter 12 and detector assembly 14 can include not only the control features discussed above, but also physical positioning controls. As will be readily understood, the subject 9 will be disposed substantially between the x-ray radiation transmitter 12 and detector assembly 14 in a spatial relation 11a with the x-ray radiation transmitter 12 and in another spatial relation 11b with the detector assembly 14, with such spatial relations 11a, 11b having three dimensions (e.g., along the x-, y- and z-axes). Accordingly, the region of interest 11 within the subject 9 will also have corresponding spatial relationships with the x-ray radiation transmitter 12 and detector assembly 14 (with such region of interest 11 being defined as that portion of the subject 9 to which the subject radiation 13a is to be applied).

As part of the control signals 17b provided to the x-ray radiation transmitter 12, additional control signals 17bc can be provided to control physical positioning of the x-ray radiation transmitter 12, e.g., through the use of some form of electromechanical assembly (not shown, but many types of which are well known in the art) for positioning the x-ray radiation transmitter 12 as desired. Similarly, additional control signals 17c can be provided to the detector assembly 14 for controlling the physical positioning of the assembly 14, e.g., via some form of conventional electromechanical assembly (not shown), for physical positioning of the detector assembly 14 as desired. Further similarly, still further control signals 17d can be provided for controlling the physical positioning of the subject (and, therefore, the physical positioning of the region of interest 11), e.g., also via some form of conventional electromechanical assembly (not shown), for positioning the physical location of the subject 9 as desired. Accordingly, the spatial relations 11a, 11b of the subject 9 (and region of interest 11) to the x-ray radiation transmitter 12 and detector assembly 14 can be controlled as desired in all three dimensions (x, y, z), thereby providing for optimum irradiation of the region of interest 11 within the subject 9.

Figure 4A:
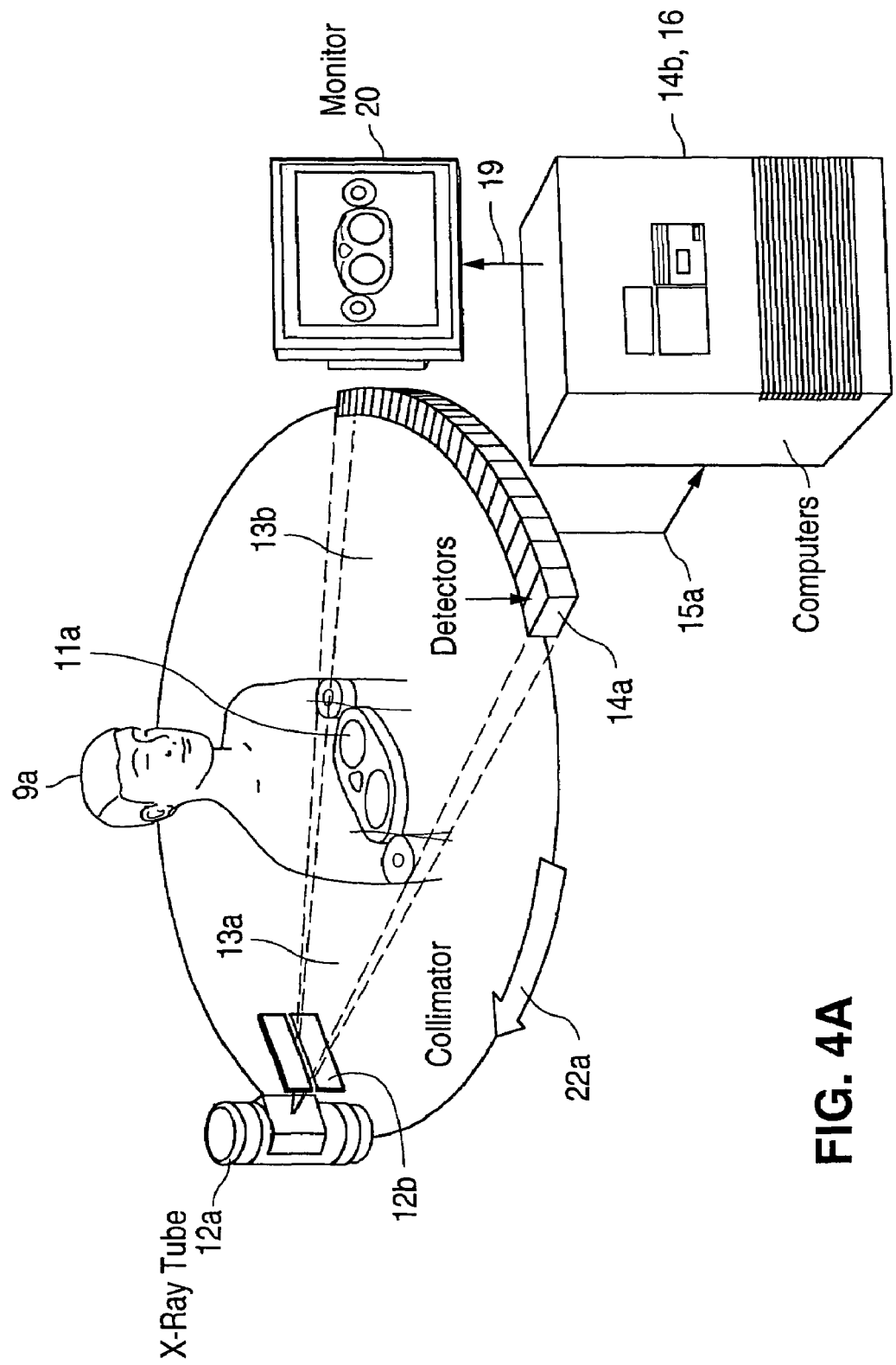
FIGS. 4A, 4B and 4C illustrate the relationships of an x-ray source, subject, detector and image reconstruction computer, and display for fan beam and cone beam CT systems.

Referring to FIG. 4A, the above-discussed technique of scanning a subject with a large field of view followed by using well-known image analysis techniques to locate a region of interest followed, in turn, by then focusing on the region of interest with a smaller field of view scan at significantly increased resolution can also be used for volumetric (i.e., three-dimension) images such as those obtained using fan beam computed tomography (CT). In accordance with well-known principles, a fan beam CT scan involves the placement of the subject 9a within a rotational arc 22a about which the x-ray source 12a and detector assembly 14a travel. A fan beam 13a of x-ray radiation is created as the x-ray source probe 12a and detector assembly 14a rotate about the subject 9a, irradiating a "slice" 11a, the thickness of which is determined by the collimator 12b. The numerous profiles, or "snapshots", of the attenuated x-ray beam 13b as collected by the detector 14a are provided to the processor 14b, as discussed above. Using well-known techniques, each profile is then backward reconstructed, or "back projected", by the processor 14b and control system 16. A monitor 20 can be used to display the image data 19 for the user (not shown).

Figure 4B:
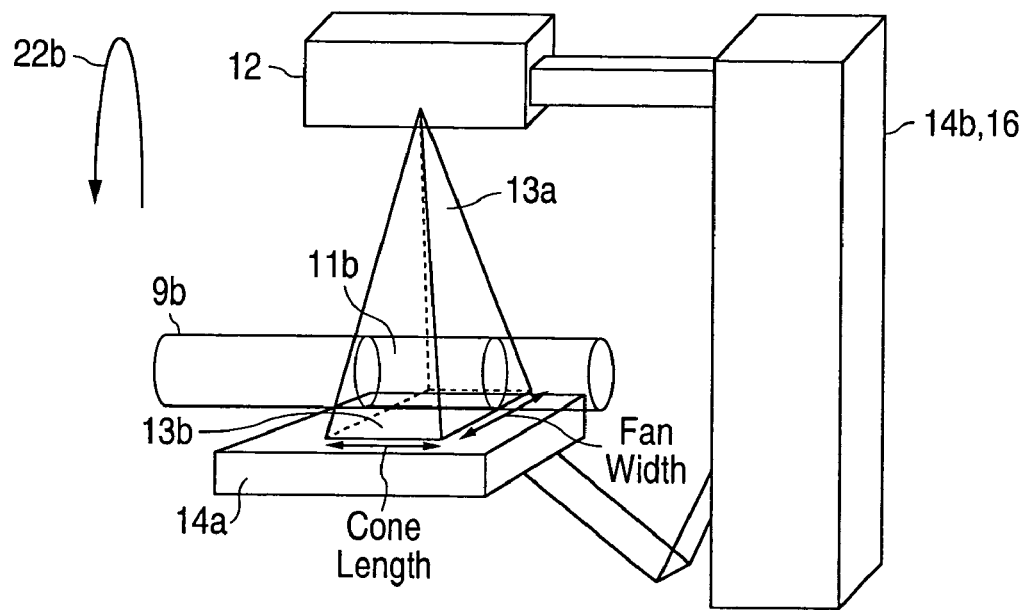

Referring to FIG. 4B, this technique of scanning a subject with a large field of view followed by using well-known image analysis techniques to locate a region of interest followed, in turn, by then focusing on the region of interest with a smaller field of view scan at significantly increased resolution can also be used for volumetric images obtained using cone beam CT. In accordance with well-known principles, a cone beam CT scan involves the placement of the subject 9b within a rotational arc 22b about which the x-ray radiation transmitter 12 and detector assembly 14a travel. A cone beam 13a of x-ray radiation is created as the x-ray radiation transmitter 12 and detector assembly 14a rotate about the subject 9b, irradiating a portion 11b of the subject, the length and width of which are determined by the cone length and fan width. The numerous profiles, or "snapshots", of the attenuated x-ray beam 13b as collected by the detector 14a are provided to the processor 14b, as discussed above. Using well-known techniques, each profile is then backward reconstructed, or "back projected", by the processor 14b and control system 16.

Figure 4C:
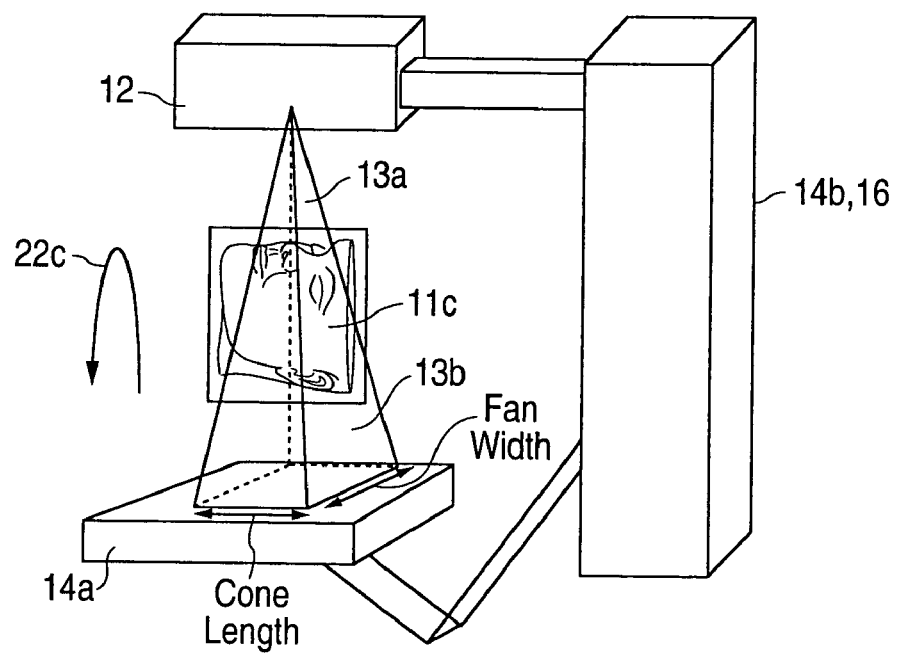
Figure 4D:
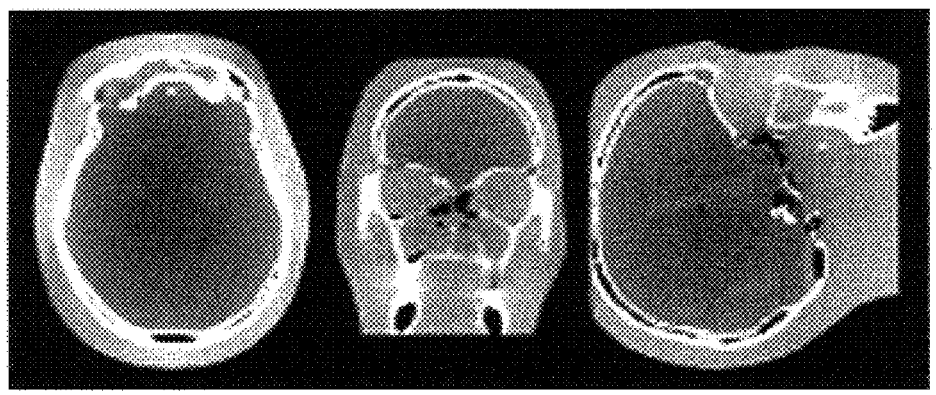
FIG. 4D illustrates x-ray images made available by the cone beam CT system of FIG. 4C.

Referring to FIGS. 4C and 4D, when applied to an anatomical subject 111c, this technique allows images from various perspectives to be obtained, within any one of which the resolution of the region of interest can then be further enhanced as discussed above.

Figure 5:
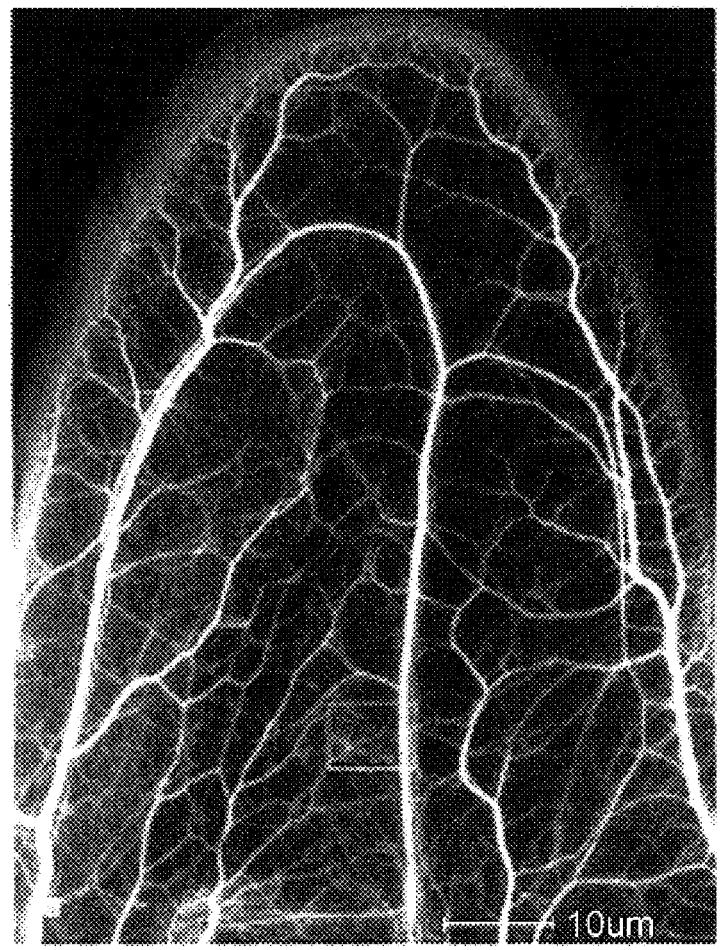
FIG. 5 illustrates an x-ray image of a tumor with no magnification.

Referring to FIG. 5, advantages of using the above-discussed technique for locating and analyzing the region of interest in the context of volumetric images can be described in accordance with the following example. A typical x-ray scan of a tumor, as shown, reveals the vascular structure. Using well-known image analysis techniques, the area bounded by the rectangle can be identified as a potential region of interest.

Figure 6:
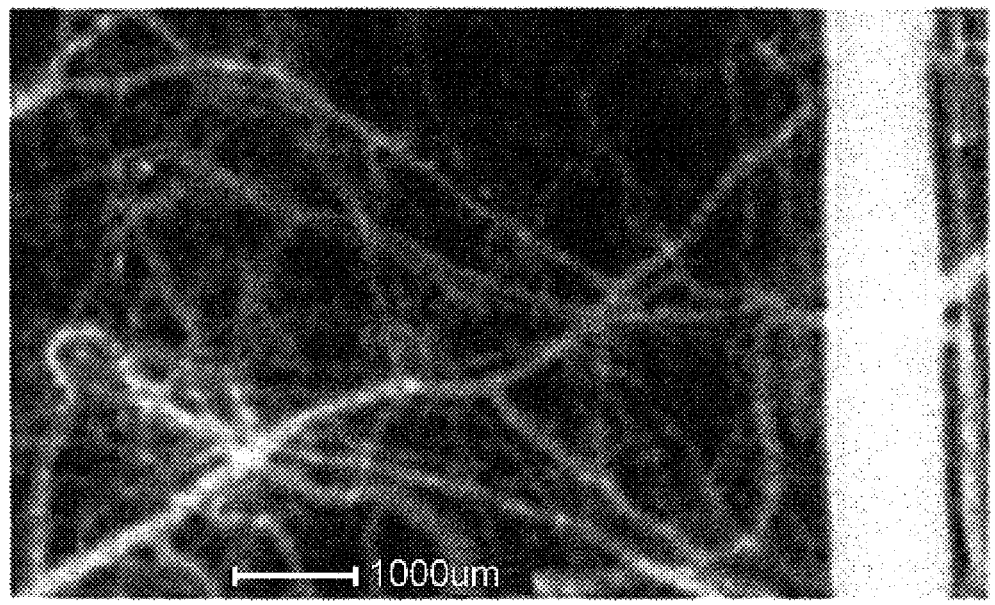
FIG. 6 illustrates the region bounded by the rectangle in FIG. 5 at increased magnification.

Referring to FIG. 6, this region of interest can then be scanned at increased resolution, as discussed above for the example of FIG. 3. However, the finer details of the vascular structure may remain difficult, if not impossible, to discern.

Figure 7:
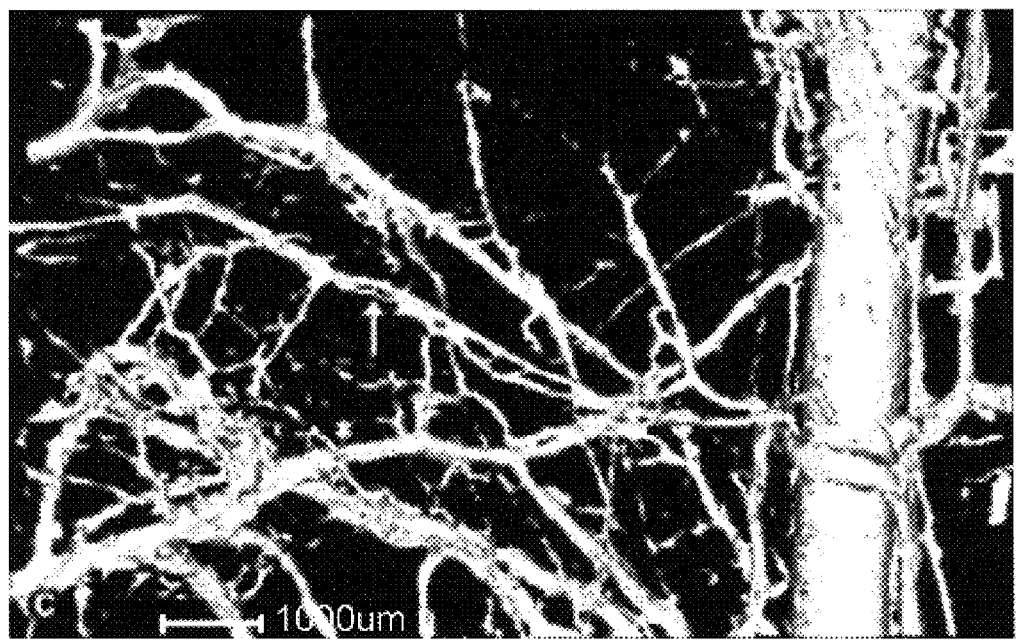
FIG. 7 illustrates the same region of interest as FIG. 6 using volumetric imaging.

Referring to FIG. 7, performing a volumetric scan on the region of interest produces significantly greater detail. For example, in the regions bounded by the upper and lower dashed circles, arteries and veins, respectively, can be distinguished.

This technique of automated image enhancement through amplification of identified regions of interest becomes more important as resolutions of electronic image sensor arrays increase. It has been determined that the maximum resolution of an image that can be perceived by the unaided human eye, e.g., without aid from any optical magnification, is approximately 121 microns of pixel pitch (due to the spacing of cones in the human retina). Typically, it is preferred to read x-rays at actual size i.e., at substantially the same size as the anatomical feature being analyzed. Additionally, as noted above, with the desire to minimize the dosage of x-rays to the patient, it is generally desirable to display and/or acquire the initial x-ray image at normal size for display on a monitor with a minimum pixel pitch of approximately 121 microns. Then, using the techniques as discussed above for image enhancement and amplification of regions of interest, the additional x-ray images acquired for the regions of interest at higher dosages can be done at the higher resolutions of which newer electronic imaging sensors are capable. Accordingly, an appropriately magnified image can then be displayed on the monitor taking advantage of such improved sensor resolution.

This technique of automated image enhancement can also be applied to images where forms of enhancement other than magnification per se are desired, such as when it is desired that the user be able to visually perceive features which are known, suspected or believed to exist within the subject of the x-ray imaging but such features do not necessarily require magnification. Instead, when such features are detected in the initial or subsequent image data, further radiation can be applied in an appropriate manner (e.g., focusing, collimation or other form of concentration) as discussed above to cause such features to become detectable by the electronic imaging sensors such that the image data produced allow such features to be visually perceived without magnification. For example, if it is desired to observe features (e.g., size, shape or contours) of the internal organs, such features can be enhanced for viewing as part of the final image without necessarily also requiring magnification of such features. While the foregoing discussion has been in the context of medical imaging, it will be readily apparent to one of ordinary skill in the art of x-ray imaging that the x-ray imaging system and method of the presently claimed invention can be readily applied outside the field of medical imaging. For example, various industrial applications that will benefit from the system and method of the presently claimed invention include, among others, non-destructive testing of physical objects (e.g., various articles or materials of manufacture) and screening of packages or cargo (e.g., in the shipping or travel industries).

Regarding non-destructive testing of physical objects, the x-ray imaging system and method of the presently claimed invention can be applied to look for defects or flaws in an article which may occur during its manufacture or handling. For example, a metal casting can be tested to determine whether any flaws, such as cracks, which are not visible to the naked eye exist by having the control system analyze the x-ray data in conjunction with data representing various models of known or suspected forms of flaws. Clearly, in this type of application, such testing can be simpler in that the amount of x-ray exposure will generally be of less concern.

Regarding package or cargo screening, the x-ray imaging system and method of the presently claimed invention can be applied by having the control system analyze the x-ray data in conjunction with data representing various objects of which any general and often specific shapes or image profiles are known.

Accordingly, an x-ray imaging system and method for automatic image resolution enhancement in accordance with the presently claimed invention can be used in virtually any application in which it would be advantageous to apply successive doses of x-ray radiation in an automated manner so as to obtain successively more detailed images of internal characteristics of the subject.

Various other modifications and alternations in the structure and method of operation of this invention will be apparent to those skilled in the art without departing from the scope and the spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An apparatus including an automated X-ray imaging system for producing a plurality of X-ray imaging signals, comprising:
    an X-ray emission system responsive to at least one emission control signal by providing at least first and second doses of X-ray radiation, wherein said second dose differs from said first dose in one or more of a plurality of X-ray radiation characteristics;
    an X-ray detection system responsive to at least one detection control signal and for placement in relation to said X-ray emission system to be responsive to at least respective portions of said first and second doses of X-ray radiation following exposure thereto of at least a portion of a subject disposed substantially between said X-ray emission and detection systems by providing corresponding first and second image signals corresponding to said respective portions of said first and second doses of X-ray radiation, respectively; and
    a control system, coupled to said X-ray emission and detection systems, responsive to said first and second image signals by providing said emission and detection control signals, wherein said second image signal differs from said first image signal in one or more of a plurality of image characteristics, and said first and second image signals together form a plurality of images which is one or more of
        a planar image and a volumetric image, respectively,
        a volumetric image and a planar image, respectively,
        a lower resolution image and a higher resolution image, respectively, and
        a higher resolution image and a lower resolution image, respectively; wherein
    said portion of said subject defines a target region for said at least respective portions of said first and second doses of X-ray radiation,
    said target region is disposed in a first spatial relation to said X-ray emission system,
    said target region is disposed in a second spatial relation to said X-ray detection system, and
    said X-ray emission system is further responsive to said at least one emission control signal by controlling said first spatial relation.

2. An apparatus including an automated X-ray imaging system for producing a plurality of X-ray imaging signals, comprising:
    an X-ray emission system responsive to at least one emission control signal by providing at least first and second doses of X-ray radiation, wherein said second dose differs from said first dose in one or more of a plurality of X-ray radiation characteristics;
    an X-ray detection system responsive to at least one detection control signal and for placement in relation to said X-ray emission system to be responsive to at least respective portions of said first and second doses of X-ray radiation following exposure thereto of at least a portion of a subject disposed substantially between said X-ray emission and detection systems by providing corresponding first and second image signals corresponding to said respective portions of said first and second doses of X-ray radiation, respectively; and
    a control system, coupled to said X-ray emission and detection systems, responsive to said first and second image signals by providing said emission and detection control signals, wherein said second image signal differs from said first image signal in one or more of a plurality of image characteristics, and said first and second image signals together form a plurality of images which is one or more of
        a planar image and a volumetric image, respectively,
        a volumetric image and a planar image, respectively,
        a lower resolution image and a higher resolution image, respectively, and
        a higher resolution image and a lower resolution image, respectively; wherein
    said portion of said subject defines a target region for said at least respective portions of said first and second doses of X-ray radiation,
    said target region is disposed in a first spatial relation to said X-ray emission system,
    said target region is disposed in a second spatial relation to said X-ray detection system, and
    said X-ray detection system is further responsive to said at least one detection control signal by controlling said second spatial relation.

3. An apparatus including an automated X-ray imaging system for producing a plurality of X-ray imaging signals, comprising:
    an X-ray emission system responsive to at least one emission control signal by providing at least first and second doses of X-ray radiation, wherein said second dose differs from said first dose in one or more of a plurality of X-ray radiation characteristics;
    an X-ray detection system responsive to at least one detection control signal and for placement in relation to said X-ray emission system to be responsive to at least respective portions of said first and second doses of X-ray radiation following exposure thereto of at least a portion of a subject disposed substantially between said X-ray emission and detection systems by providing corresponding first and second image signals corresponding to said respective portions of said first and second doses of X-ray radiation, respectively; and
    a control system, coupled to said X-ray emission and detection systems, responsive to said first and second image signals by providing said emission and detection control signals, wherein said second image signal differs from said first image signal in one or more of a plurality of image characteristics, and said first and second image signals together form a plurality of images which is one or more of
        a planar image and a volumetric image, respectively,
        a volumetric image and a planar image, respectively, a lower resolution image and a higher resolution image, respectively, and a higher resolution image and a lower resolution image, respectively; wherein said portion of said subject defines a target region for said at least respective portions of said first and second doses of X-ray radiation, said target region is disposed in a first spatial relation to said X-ray emission system, said target region is disposed in a second spatial relation to said X-ray detection system, said X-ray emission system is further responsive to said at least one emission control signal by controlling said first spatial relation, and said X-ray detection system is further responsive to said at least one detection control signal by controlling said second spatial relation.

4. An apparatus including an automated X-ray imaging system for producing a plurality of X-ray imaging signals, comprising:

an X-ray emission system responsive to at least one emission control signal by providing at least first and second doses of X-ray radiation, wherein said second dose differs from said first dose in one or more of a plurality of X-ray radiation characteristics, and said X-ray emission system includes an X-ray source responsive to a first portion of said at least one emission control signal by providing X-ray radiation with at least one of said plurality of X-ray radiation characteristics corresponding to said first portion of said at least one emission control signal, and a collimator coupled to said X-ray source and responsive to a second portion of said at least one emission control signal by conveying said X-ray radiation with at least another of said plurality of X-ray radiation characteristics corresponding to said second portion of said at least one emission control signal;

an X-ray detection system responsive to at least one detection control signal and for placement in relation to said X-ray emission system to be responsive to at least respective portions of said first and second doses of X-ray radiation following exposure thereto of at least a portion of a subject disposed substantially between said X-ray emission and detection systems by providing corresponding first and second image signals corresponding to said respective portions of said first and second doses of X-ray radiation, respectively; and a control system, coupled to said X-ray emission and detection systems, responsive to said first and second image signals by providing said emission and detection control signals, wherein said second image signal differs from said first image signal in one or more of a plurality of image characteristics, and said first and second image signals together form a plurality of images which is one or more of a planar image and a volumetric image, respectively, a volumetric image and a planar image, respectively, a lower resolution image and a higher resolution image, respectively, and a higher resolution image and a lower resolution image, respectively.

5. A automated method for producing a plurality of X-ray imaging signals corresponding to selected views of a subject with selectively variable image resolutions, comprising:

receiving at least one emission control signal;

generating, in response to said at least one emission control signal, at least first and second doses of X-ray radiation, wherein said second dose differs from said first dose in one or more of a plurality of X-ray radiation characteristics, by generating with an X-ray emission system, in response to said at least one emission control signal, at least first and second doses of X-ray radiation;

receiving at least respective portions of said first and second doses of X-ray radiation following exposure thereto of at least a portion of a subject by receiving with an X-ray detection system at least respective portions of said first and second doses of X-ray radiation following exposure thereto of at least a portion of a subject disposed substantially between said X-ray emission and detection systems, wherein said portion of said subject defines a target region for said at least respective portions of said first and second doses of X-ray radiation;

receiving at least one detection control signal;

generating, in response to said at least one detection control signal and said at least respective portions of said first and second doses of X-ray radiation, first and second image signals corresponding to said respective portions of said first and second doses of X-ray radiation, respectively;

processing said first and second image signals;

generating, in response to said processed first and second image signals, said emission and detection control signals, wherein said second image signal differs from said first image signal in one or more of a plurality of image characteristics, and said first and second image signals together form a plurality of images which is one or more of a planar image and a volumetric image, respectively, a volumetric image and a planar image, respectively, a lower resolution image and a higher resolution image, respectively, and a higher resolution image and a lower resolution image, respectively;

disposing said target region in a first spatial relation to said X-ray emission system;

disposing said target region in a second spatial relation to said X-ray detection system; and controlling said first spatial relation in further response to said at least one emission control signal.

6. A automated method for producing a plurality of X-ray imaging signals corresponding to selected views of a subject with selectively variable image resolutions, comprising:

receiving at least one emission control signal;

generating, in response to said at least one emission control signal, at least first and second doses of X-ray radiation, wherein said second dose differs from said first dose in one or more of a plurality of X-ray radiation characteristics, by generating with an X-ray emission system, in response to said at least one emission control signal, at least first and second doses of X-ray radiation;

receiving at least respective portions of said first and second doses of X-ray radiation following exposure thereto of at least a portion of a subject by receiving with an X-ray detection system at least respective portions of said first and second doses of X-ray radiation following exposure thereto of at least a portion of a subject disposed substantially between said X-ray emission and detection systems, wherein said portion of said subject defines a target region for said at least respective portions of said first and second doses of X-ray radiation;

receiving at least one detection control signal;

generating, in response to said at least one detection control signal and said at least respective portions of said first and second doses of X-ray radiation, first and second image signals corresponding to said respective portions of said first and second doses of X-ray radiation, respectively;

processing said first and second image signals;

generating, in response to said processed first and second image signals, said emission and detection control signals, wherein said second image signal differs from said first image signal in one or more of a plurality of image characteristics, and said first and second image signals together form a plurality of images which is one or more of a planar image and a volumetric image, respectively,
a volumetric image and a planar image, respectively,
a lower resolution image and a higher resolution image, respectively, and
a higher resolution image and a lower resolution image, respectively;

disposing said target region in a first spatial relation to said X-ray emission system;

disposing said target region in a second spatial relation to said X-ray detection system; and controlling said second spatial relation in further response to said at least one detection control signal.

7. A automated method for producing a plurality of X-ray imaging signals corresponding to selected views of a subject with selectively variable image resolutions, comprising:

receiving at least one emission control signal;

generating, in response to said at least one emission control signal, at least first and second doses of X-ray radiation, wherein said second dose differs from said first dose in one or more of a plurality of X-ray radiation characteristics, by generating with an X-ray emission system, in response to said at least one emission control signal, at least first and second doses of X-ray radiation;

receiving at least respective portions of said first and second doses of X-ray radiation following exposure thereto of at least a portion of a subject by receiving with an X-ray detection system at least respective portions of said first and second doses of X-ray radiation following exposure thereto of at least a portion of a subject disposed substantially between said X-ray emission and detection systems, wherein said portion of said subject defines a target region for said at least respective portions of said first and second doses of X-ray radiation;

receiving at least one detection control signal;

generating, in response to said at least one detection control signal and said at least respective portions of said first and second doses of X-ray radiation, first and second image signals corresponding to said respective portions of said first and second doses of X-ray radiation, respectively;

processing said first and second image signals;

generating, in response to said processed first and second image signals, said emission and detection control signals, wherein said second image signal differs from said first image signal in one or more of a plurality of image characteristics, and said first and second image signals together form a plurality of images which is one or more of a planar image and a volumetric image, respectively,
a volumetric image and a planar image, respectively,
a lower resolution image and a higher resolution image, respectively, and
a higher resolution image and a lower resolution image, respectively;

disposing said target region in a first spatial relation to said X-ray emission system;

disposing said target region in a second spatial relation to said X-ray detection system;

controlling said first spatial relation in further response to said at least one emission control signal; and controlling said second spatial relation in further response to said at least one detection control signal.

8. A automated method for producing a plurality of X-ray imaging signals corresponding to selected views of a subject with selectively variable image resolutions, comprising:

receiving at least one emission control signal;

generating, in response to said at least one emission control signal, at least first and second doses of X-ray radiation, wherein said second dose differs from said first dose in one or more of a plurality of X-ray radiation characteristics, by generating, in response to a first portion of said at least one emission control signal, X-ray radiation with at least one of said plurality of X-ray radiation characteristics corresponding to said first portion of said at least one emission control signal, and collimating, in response to a second portion of said at least one emission control signal, said X-ray radiation;

receiving at least respective portions of said first and second doses of X-ray radiation following exposure thereto of at least a portion of a subject;

receiving at least one detection control signal;

generating, in response to said at least one detection control signal and said at least respective portions of said first and second doses of X-ray radiation, first and second image signals corresponding to said respective portions of said first and second doses of X-ray radiation, respectively;

processing said first and second image signals; and generating, in response to said processed first and second image signals, said emission and detection control signals, wherein said second image signal differs from said first image signal in one or more of a plurality of image characteristics, and said first and second image signals together form a plurality of images which is one or more of a planar image and a volumetric image, respectively,
a volumetric image and a planar image, respectively,
a lower resolution image and a higher resolution image, respectively, and
a higher resolution image and a lower resolution image, respectively.

9. The method of claim 8, wherein said generating, in response to said at least one detection control signal and said at least respective portions of said first and second doses of X-ray radiation, first and second image signals comprises generating, in response to a first portion of said at least one detection control signal, a plurality of pixel signals.

10. The method of claim 9, wherein said generating, in response to said at least one detection control signal and said at least respective portions of said first and second doses of X-ray radiation, first and second image signals further comprises processing said plurality of pixel signals to generate said first and second image signals.

* * * * *